United States Patent
Deshpande et al.

(10) Patent No.: US 6,388,070 B1
(45) Date of Patent: May 14, 2002

(54) THIOESTER DERIVATIVES OF THIAZOLYL ACETIC ACID AND THEIR USE IN THE PREPARATION OF CEPHALOSPORIN COMPOUNDS

(75) Inventors: Pandurang Balwant Deshpande; Parven Kumar Luthra, both of Tamilnadu (IN)

(73) Assignee: Orchid Chemicals & Pharmaceuticals Ltd., Tamil Nadu (IN)

( * ) Notice: Subject to any disclaimer, the term of this patent is extended or adjusted under 35 U.S.C. 154(b) by 0 days.

(21) Appl. No.: 09/754,302

(22) Filed: Jan. 5, 2001

(51) Int. Cl.$^7$ .................. C07D 417/12; C07D 501/04; C07D 501/46; C07D 501/36
(52) U.S. Cl. ............... 540/227; 540/222; 540/225; 540/228; 548/144
(58) Field of Search .................. 540/222, 227, 540/228; 548/144

(56) References Cited

U.S. PATENT DOCUMENTS 5,869,649 A * 2/1999 Khanna .................. 540/227

OTHER PUBLICATIONS

Merck Index, 12$^{th}$ Edition, #1995 (1996).*
Green et al, "Protective Groups in Organic Synthesis", vol. 3, abbreviations list (undated).*

* cited by examiner

Primary Examiner—Mark L. Berch
(74) Attorney, Agent, or Firm—Burns, Doane, Swecker & Mathis, L.L.P.

(57) ABSTRACT

The present invention provides novel thioester derivatives of thiazolyl acetic acid of the general formula (I),

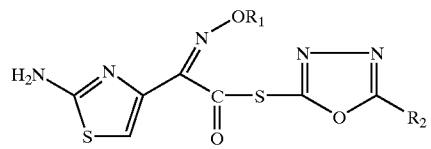

(I)

wherein, $R_1$ represents H, trityl, $CH_3$, or $CR_aR_bCOOR_3$, in which $R_a$ and $R_b$, independently of one another, represents hydrogen or methyl and $R_3$ represents H or $C_1$–$C_7$ alkyl; and $R_2$ represents $C_1$–$C_4$ alkyl or phenyl. The invention also provides a method for preparation of the thioester derivatives and reaction of the thioester derivatives with cephem carboxylic acids to produce cephalosporin antibiotic compounds having general formula (II),

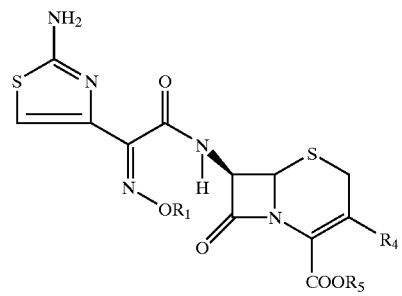

(II)

wherein, $R_1$ represents H, trityl, $CH_3$, or $CR_aR_bCOOR_3$, in which $R_a$ and $R_b$, independently of one another, represents hydrogen or methyl and $R_3$ represents H or $C_1$–$C_7$ alkyl; $R_4$ is $CH_3$, —CH=$CH_2$, $CH_2OCH_3$, $CH_2OCOCH_3$,

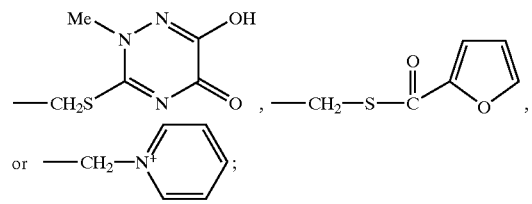

or —$CH_2$—N⁺(pyridyl);

and $R_5$ is H or a salt or a carboxylic protecting group, comprising, acylating a compound of formula (III),

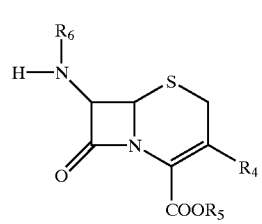

(III)

wherein, $R_4$ and $R_5$ are defined as above, and $R_6$ is H or trimethylsilyl;
with a compound of formula (I).

14 Claims, No Drawings

THIOESTER DERIVATIVES OF THIAZOLYL ACETIC ACID AND THEIR USE IN THE PREPARATION OF CEPHALOSPORIN COMPOUNDS

FIELD OF INVENTION

The present invention relates to novel thioester derivatives of thiazolyl acetic acid of the general formula (I). The invention also relates to a novel process for preparation of the thioester derivatives. The reactive thioester derivatives are useful as intermediate for the preparation of cephalosporin antibiotics having the formula (II). In addition, the present invention also relates to a process for preparation of cephalosporin antibiotics using the said thioester derivatives.

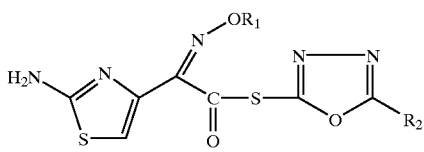

(I)

wherein, $R_1$ represents H, trityl, $CH_3$, $CR_aR_bCOOR_3$ ($R_a$ and $R_b$ independently of one another represents hydrogen or methyl and $R_3$ represents H or $C_1$–$C_7$ alkyl).

$R_2$ represents $C_1$–$C_4$ alkyl or phenyl.

BACKGROUND OF THE INVENTION

Acid chlorides, anhydrides, esters, amide etc. are reported in the chemical literature for activation of carboxylic acid of formula (IV). Activation in the form of acid chloride required protection and deprotection of $NH_2$ group.

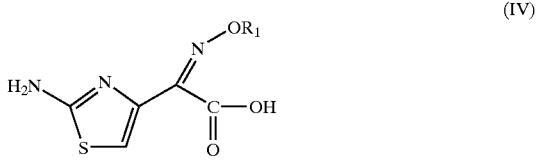

(IV)

Activation of acid (IV) is reported by $SO_2Cl_2$/DMF in U.S. Pat. No. 5,856,502 and $SOCl_2$/DMF in U.S. Pat. No. 5,037,988. These processes suffer the limitation of using harmful and pungent smelling chemicals like $SOCl_2$, $SO_2Cl_2$ along with solvents like benzene, toluene, etc. and stringent conditions required for carrying out the reactions at commercial scale.

In U.S. Pat. Nos. 4,576,749 and 4,548,748 the acid of formula (IV) have also been activated by reacting with 1-hydroxybenzotriazole (HOBT) or 2-mercaptobenzothiazole (MBT) in the presence of dicyclohexylcarbodiimide (DCC) to produce reactive ester of the acid (IV) which then reacted to cephem moiety to prepare cephem antibiotics, but the processes are time consuming and with low yields, hence not suitable.

U.S. Pat. No. 4,767,852 discloses a process for production of cephems by acylating 7-amino-3-cephem-4-carboxylic acid with 2-mercaptobenzothiazolyl-(Z)-2-(2-aminothiazol-4-yl)-2-methoxyiminoacetate (MAEM). Similarly, U.S. Pat. No. 5,026,843 (1991) disclosed a process for preparing ceftriaxone disodium hemiheptahydrate by acylation of ACT by using MAEM as acylating agents in good yield and quality. Thus MAEM has become the standard acylating agent for the preparation of cephalosporins having an oximino group and a 2-aminothiazolyl group in 7-position of cephem compounds.

However, the synthesis of MAEM from acid (III) and 2,2'-dithio-bis-benzothiazole involves use of costly condensing agent triphenylphosphine (TPP). Moreover, during condensation of MAEM with 7-amino-3-cephem-4-carboxylic acid compound (III), a toxic compound MBT is also produced as a byproduct, see e.g., Chemical Abstracts, 111, 19243$_P$ (1989) which is difficult to remove completely.

Thus it is evident that the procedures described in the prior art for preparation of these antibiotics are complex, involving protection, deprotection and are associated with toxic byproduct generation. Hence there is a need to develop new acylating agents which are capable of transferring the 2-aminothiazolyl moiety to cephem compounds of formula (III) in good yield but without producing this toxic byproduct. On the similar lines, a new thioester was reported by D. G. Walker, Tet. Lett. 1990, 31, 6481 to, acylate the cephem moiety to get cefepime sulfate but yields obtained by using this thioester were in the range of 54–73% which cannot be considered as good yield to operate a process at commercial scale. The use of this thioester was reported in the Tet. Lett. 1990, 31, 6481 only for cefepime and not for other cephalosporins. This thioester was exploited in U.S. Pat. No. 5,869,649 for making three other important cephem antibiotics.

OBJECTIVES OF THE INVENTION

The primary objective of the invention is to prepare novel thioester derivatives of thiazolyl acetic acid of the general formula (I), which would be better than the existing reactive derivatives and suitable for being used in the manufacture of cephalosporin antibiotics.

Another objective of the present invention is to provide a process for the synthesis of thioester derivatives of formula (I) from thiazolyl acetic acid of the general formula (IV) and thio-oxadiazoles of the general formula (VI).

Yet another objective of the present invention is to provide a simple, high yielding and cost-effective process for the preparation of cephalosporin antibiotics of the general formula (II).

Still another objective of the present invention is to produce cephalosporin antibiotics that are highly pure and free from toxic byproducts.

One more objective of the present invention is to provide a process for the preparation of cephalosporin antibiotics of the general formula (II) from the said novel thioester derivatives.

SUMMARY OF THE INVENTION

The present invention provides novel thioester derivatives of thiazolyl acetic acid of the general formula (I). The invention also provides a method by which, the said thioester derivatives can be prepared. The thioester derivatives so obtained are reacted with 7-amino-cephem carboxylic acids of the general formula (III) to produce cephalosporin antibiotic compounds having the general formula (II).

DETAILED DESCRIPTION OF THE INVENTION

The present invention provides new thioesters of the general formula (I) that are prepared by a novel method which has not been reported in the prior art. The use of these compounds in the process for preparing cephem derivatives renders the process entirely new and different from others. The novel derivative of thiazolyl acetic acid is represented by the formula (I)

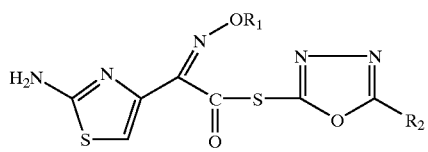
(I)

wherein, $R_1$ represents H, trityl, $CH_3$, $CR_aR_bCOOR_3$ ($R_a$ and $R_b$ independently of one another represents hydrogen or methyl and $R_3$ represents H or $C_1$–$C_7$ alkyl).

$R_2$ represents $C_1$–$C_4$ alkyl or phenyl

The synthesis of compound (I) is achieved by reacting thiazolyl acetic acid of the general formula (IV) with thiooxadiazoles of the general formula (VI) in organic solvent in presence of an organic base. The condensation is done with the help of a condensation agent of the formula (V). When the above reaction is carried out, the temperature is maintained between −10° and +30° C.

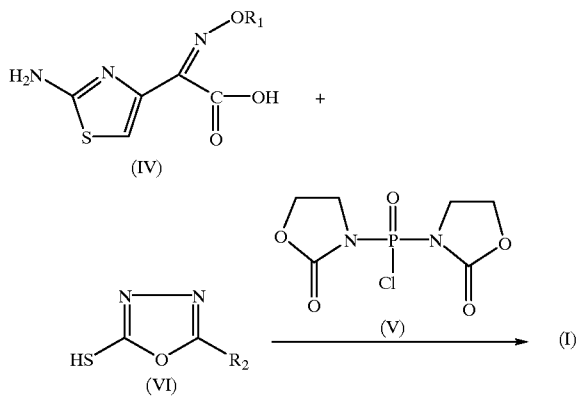

wherein, $R_1$ represents H, trityl, $CH_3$, $CR_aR_bCOOR_3$ ($R_a$ and $R_b$ independently of one another represents hydrogen or methyl and $R_3$ represents H or $C_1$–$C_7$ alkyl).

$R_2$ represents $C_1$–$C_4$ alkyl or phenyl

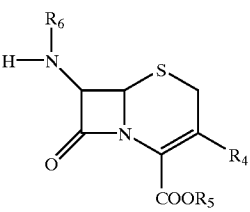
(III)

wherein $R_4$ is $CH_3$, —CH=$CH_2$, $CH_2OCH_3$, $CH_2OCOCH_3$,

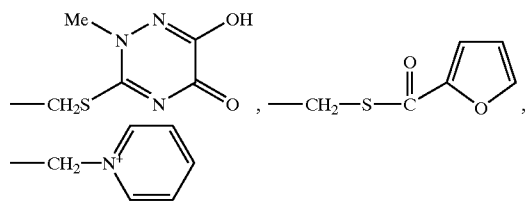

or a standard cephalosporin substituent.

$R_5$ is hydrogen, salt or carboxylic protecting group.

$R_6$ is hydrogen or silyl.

In an embodiment the organic solvent is selected from the group comprising dichloromethane, tetrahydrofuran, dioxane, N,N-dimethylformamide, acetone, carbon tetrachloride and mixtures thereof.

In another embodiment the condensation agent is bis-(2-oxo-oxazolidinyl) phosphinic chloride.

In still another embodiment the organic base is selected from triethylamine diethylamine, tributylamine, pyridine, N-alkylanilines, 1,8-diazabicyclo[5.4.2]undec-7-ene, 1,5-diazabicyclo[4.3.0]non-5-ene, N-methylmorpholine and mixtures thereof.

The compound (I) so obtained is reacted with 7-amino cephem carboxylic acids of the general formula (III) in organic solvent in presence of organic base to obtain cephalosporin antibiotics of general formula (II).

For protection of carboxylic group as ester, following group can be used which are easily converted into free carboxylic acid, e.g. p-methoxybenzyl, p-nitrobenzyl, diphenyl methyl, phenacyl trimethylsilyl.

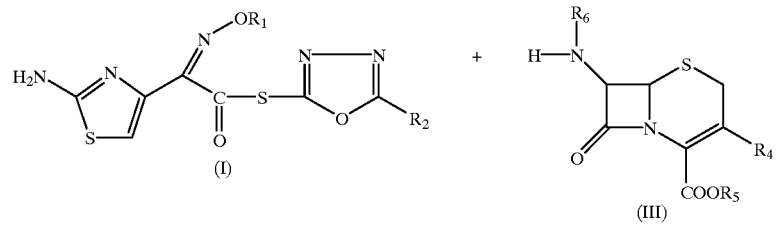

-continued

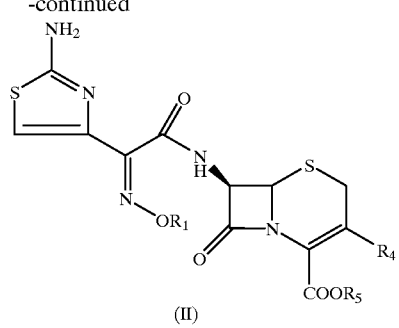

(II)

wherein, $R_1$, $R_2$ $R_4$, $R_5$, & $R_6$ are as defined above.

The present invention provides a method by which cephalosporin antibiotics are obtained in high purity (95–99%) and excellent yield (79–95%) without the necessity for protecting the amino group of the acylating agents and the production of toxic byproduct namely 2-mercaptobenzothiazole is avoided.

The substituent $R_4$ in cephem compound (III) represents methyl, acetyloxymethyl, methoxymethyl, vinyl, pyridylmethyl, propenyl, 2,5-dihydro-6-hydroxy-2-methyl-5-oxo-1,2,4-triazine-3-thiol, furanyl-2-carbonyl thiol or a standard cephalosporin substituents defined by $R_4$. In general, $R_4$ represents —$CH_2$—X wherein X is a residue of any organic or inorganic nucleophilic compound, e.g., halogen, hydroxy, cyano, mercapto, azido, amino, etc. Furthermore, X may preferably represent residue of any 5 or 6 membered heterocyclic thiol.

The heterocyclic thiol contains one to four hetero atoms selected from a group of nitrogen, oxygen and/or sulfur. Some of the examples of five membered ring are 1,2,4-thiadiazolyl, 1,3,4-thiadiazolyl, 1H-tetrazolyl, 1,2,4-tetrazolyl, 1,2,3-tetrazolyl, 1,3,4-oxadiazolyl, 1,2,4-oxadiazolyl, etc. The six membered heterocyclic ring can be exemplified by pyridyl, pyrimidyl, pyridinyl-N-oxide, etc.

$R_5$ represents hydrogen, salt or a standard carboxylic protecting group.

$R_6$ is hydrogen or silyl.

The condensation of cephem compound (III) with thioester (I) is performed by two different methodologies (a) by acylating the compound (III) (when $R_6$ is H) with compound (I) in aqueous organic solvent; (b) by acylating compound (III) (when $R_6$ is silyl) with compound (I) in aprotic organic solvents. Both the approaches are comparable and afforded excellent yields and purities of cephem antibiotics (II).

Acylation of compounds of formula (III) (when $R_6$ is H) is performed in presence of a water miscible solvent like tetrahydrofuran (THF), acetonitrile, acetone, dioxane, N,N-dimethylformamide etc. but the preferable solvents are THF and acetonitrile.

In an embodiment of the present invention, acylation of compound of formula (III) (when $R_6$ is silyl) is carried out in aprotic organic solvents like halogenated hydrocarbons, toluene, alkyl ethers etc., but the preferred solvent is dichloromethane. Suitable silylating agents used for the reaction are hexamethyldisalazane, bis(trimethyl)silylacetamide and trimethylsilyl chloride.

In another embodiment of the present invention, the organic base may be selected from triethylamine, diethylamine, tributylamine, N-alkylpyridine, N-alkylanilines, 1,8-diazabicyclo[5.4.2]undec-7-ene, 1,5-diazabicyclo[4.3.0]non-5-ene, N-methylmorpholine, 1,4-diazabicyclo[2.2.2]octane, 4-dimethylamino pyridine and mixtures thereof.

The utility of the novel thioesters of 2-mercapto-5-phenyl-1,3,4-oxadiazole was tried in various coupling reactions of carboxylic acids and amines. Most of amide formation reactions have shown good results. L-alanine, 5-methylisoxazole-4-carboxylic acid, 2-thienylacetic acid, etc. are some of the compounds, which have been activated by above mentioned thiol. Few results are summarized in the following table.

| S. No. | Acids | Amines | % by HPLC |
|---|---|---|---|
| 1. | $H_2N$—CH(CH$_3$)—COOH | (pyrrolidine with NH, H, COOH) | 70–88% |
| 2. | (isoxazole-COOH, CH$_3$) | (aniline with NH$_2$, CF$_3$) | 90–97% |
| 3. | (thiophene-CH$_2$COOH) | 7-Aminocephalosporanic acid | 80–90% |

In an embodiment, $R_4$ represents any of methyl, vinyl, methoxymethyl, pyridylmethyl, acetyloxymethyl, (2,5-dihydro-6-hydroxy-2-methyl-5-oxo-1,2,4-triazin-3-yl) thiomethyl, furylcarbonyl thiomethyl or a standard cephalosporin substituent.

In another embodiment, $R_1$ represents H, trityl, $CH_3$, $CR_aR_bCOOR_3$ ($R_a$ and $R_b$ independently of one another represents hydrogen or methyl and $R_3$ represents H or $C_1$–$C_7$ alkyl).

In still another embodiment, $R_5$ is hydrogen or alkali metal salt.

In yet another embodiment, the alkali metal salts are selected from sodium, potassium and lithium salts.

In another embodiment, the compound of formula II is a syn isomer.

In still another embodiment, $R_6$ is silyl, the acylation is achieved by doing the reaction in aprotic organic solvent like halogenated hydrocarbon, toluene, alkyl ether preferably in dichloromethane.

In another embodiment, $R_2$ is methyl and $R_4$ represents any of (2,5-dihydro-6-hydroxy-2-methyl-5-oxo-1,2,4-triazin-3-yl)thiomethyl, and purification of this compound is achieved by dissolving the crude product in mixture of water and water miscible organic solvent selected from acetone, IPA, dioxane and mixture thereof.

In another embodiment, the organic base is selected from the group consisting of triethylamine, N-methylmorpholine, N-methylpyridines, N-methylanilines, 1,5-diazabicyclo [4.3.0] non-5-ene, 1,4-diazabicyclo[2.2.2]octane, 4-dimethylaminopyridine, and mixtures thereof.

In an embodiment, $R_2$ is methyl, $R_4$ is (2,5-dihydro-6-hydroxy-2-methyl-5-oxo-1,2,4-triazin-3-yl)thiomethyl, the colour impurities are separated at −10° C. to 0° C. and precipitation by water miscible organic solvent selected from acetone, IPA, dioxane and mixture thereof.

Thus the present invention provides novel thioester derivatives of thiazolyl acetic acid of the general formula (I), also, the invention provides a method by which the said thioester derivatives can be prepared by reacting thiazolyl acetic acid of the general formula (IV) with 2-mercapto-5-substituted-1,3,4-oxadiazole of the general formula (VI) (preparation of VI, J. Am. Chem. Soc., 1955, 77, 400) in a solvent, in presence of an organic base and with the help of condensation agent bis- (2-oxo-oxazolidinyl) phosphinic chloride of the formula (V) (preparation of V, Synthesis, 1980, 547). The so obtained thioester derivatives are reacted with 7-amino-cephem carboxylic acids of the general formula (III) to produce cephalosporin antibiotic compounds having the general formula (II). The cephalosporin antibiotics so obtained are of high purity (95–99%). The method gives an excellent yield (79–95%) of cephalosporin without necessitating for the protection of the amino group of the acylating agents, and the toxic byproduct 2-mercaptobenzothiazole is not produced.

Many other beneficial results can be obtained by applying disclosed invention in a different manner or by modifying the invention with the scope of disclosure. However, since the major characteristic feature of the present invention resides in the use of novel reactive thioester derivatives of thiazolyl acetic acid of the general formula (I) in preparing the cephalosporin antibiotics, the technical scope of the present invention should not be limited to the following examples.

The following examples are provided to illustrate but not to limit the claimed invention.

EXAMPLES

Example-I

Synthesis of 2-Mercapto-5-phenyl-1,3,4-oxadiazolyl-(Z)-2-(2-aminothiazol-4-yl)-2-methoxyimino Acetate (I)

(Z)-(2-aminothiazol-4-yl)methoxyimino acetic acid (20.1 g), triethylamine (22.2 g) were suspended in dry dichloromethane (150 ml), and then bis-(2-oxo-oxazodinyl) phosphinic chloride (25.4 g) was added in one lot at 0–5° C. and stirred for 1 hr. The 2-mercapto-5-phenyl-1,3,4-oxadiazole (21.3 g) was added at 0–5° C. The reaction mixture was stirred for 34 hours. After the reaction was complete, distilled water 100 ml was added to the reaction solution and the mixture was stirred for 10 min. The organic layer was separated and washed successively with 2% aq. solution bicarbonate solution (100×2 ml) and saturated saline (100 ml), dried over sodium sulphate, filtered and then concentrated under reduced pressure. To the residue, IPE (isopropyl ether) (300 ml) was added and solid was filtered, washed with IPE (100 ml). Dried to obtain 30.6 g (yield 85%) of the title compound as light yellow solid.

Melting point: 109–110° C. $^1$HNMR (DMSO-$d_6$): 83.90 (3H,s,N—OCH$_3$), 7.11(1H,s, thiazole ring proton), 7.29(2H, bs,NH$_2$), 7.6–7.9(5H, m, —C$_6$H$_5$); $^{13}$C-NMR(Acctone-$d_6$): δ 63.16, 108.7, 122.1, 129.7, 132.6, 133.7, 141.6, 146.75, 159.3, 159.6, 169.7, 173.1.

Example-II

Synthesis of 2-Mercapto-5-methyl-1,3,4-oxadiazolyl-(Z)-2-(2-aminothiazol-4-yl)-2-methoxyimino Acetate (Z)-(2-Aminothiazol-4-yl)methoxyimino acetic acid (20.1 g), triethylamine (22.2 g) were suspended in dry dichloromethane (150 ml), and then bis-(2-oxo-oxazodinyl) phosphinic chloride (25.4 g) was added in one lot at 0–5° C. and stirred for 1 hr. The 2-mercapto-5-methyl-1,3,4-oxadiazole (13.0 g) was added at 0–5° C. The reaction mixture was stirred for 34 hours and worked up in the same way as described in example-I to obtain 25.8 g (yield 84%) of the title compound as light yellow solid.

Melting point: 80–81° C. $^1$HNMR (DMSO-$d_6$): δ 2.42 (3H,s,CH$_3$), 3.8(3H,s,OCH$_3$), 7.06(1H,s,thiazole ring), 7.3 (2H,bs,NH$_2$); $^{13}$C-NMR (DMSO-$d_6$): δ 11.8, 67.9, 109.0, 141.0, 146.9, 160.0, 161.5, 169.8, 173.7.

Example-III

Synthesis of 2-mercapto-5-methyl-1,3,4-oxadiazolyl-(Z)-2-(2-aminothiazol-4-yl)-2-(methoxycarbonyl)-methoxyimino Acetate (Z)-2-(2-aminothiazol-4-yl)-(methoxycarbonyl) methoxyimino acetic acid (3.88 g) was suspended in dichloromethane (40 ml), TEA (triethylamine) (3.33 g) was added at 0°–10° C. followed by addition of bis-(2-oxo-oxazolidinyl)phosphinic chloride (3.81 g). The mixture was stirred for 1 hr. and 2-mercapto-5-phenyl-1,3,4-oxadiazole (2.6 g) was added. The reaction was monitored by HPLC. After completion of reaction, it was worked up as described in example I, to obtain 4.5 g (72%) title compound as yellow solid.

Melting point: 115–117° C. $^1$H-NMR: δ 3.61(3H,s,—COOCH$_3$), 4.79(2H,s,—OCH$_2$—CO), 7.14(1H,s,thiazole H), 7.34(2H,bs,NH$_2$), 7.6–7.9 (5H,m,—C$_6$H$_5$); $^{13}$C-NMR: δ 52.6, 72.1, 109.9, 111.1, 127.4, 129.8, 133.8, 141.1, 147.7, 159.3, 159.9, 169.4, 166.7.

Example-IV

7-[[(Z)-2-(2-Aminothiazol-4-yl)2-methoxyimino] acetamido]-3-[[(2,5-dihydro-6-hydroxy-2-methyl-5-oxo-1,2,4-triazin-3-yl)thio]methyl]-3-cephem-4-carboxylic Acid Disodium Hemiheptahydrate (Ceftriaxone Sodium)

7-Amino-3-[[(2,5-dihydro-6-hydroxy-2-methyl-5-oxo-1, 2,4-triazin-3yl)thio]methyl]3-cephem-4-carboxylic acid (20.0 g) and 2-mercapto-5-phenyl-1,3,4-oxadiazolyl-(Z)-2-(2-aminothiazol-4-yl) 2-methoxyiminoacetate (23.3 g) were suspended in a mixture of THF (180 ml), H$_2$O (80 ml) and DMAc (dimethyl acetamide) (30 ml) maintained at 0°–1° C. under stirring. Triethylamine (11.9 ml) was added in 2–3 hours at 5° C. maintaining the pH 7.5–8.5. The reaction progress was monitored by HPLC. After the reaction was complete, the mixture was extracted with dichloromethane (3×100 ml). The aq. layer was separated and treated with charcoal (0.2 g). A solution of sodium-2-ethylhexanoate (30.5 g) in acetone was added to filtrate at 10–15° C. and stirred for 1.5 hours (400 ml) of acetone was added in 1 hour at 10–15° C. to complete the crystallization. The product was filtered under N$_2$ atmosphere and wet cake was dissolved in mixture of water and acetone (1:2), and cooled to −10° C. Coloured impurities were separated. The solution was decanted and diluted with acetone (600 ml) at 18–20° C. Precipitated solid was filtered under N$_2$ and washed with acetone (20 ml). Dried under vacuum at 40–45° C. to get pure Ceftriaxone sodium, 28.5 g (yield 89%).

HPLC (purity): 99.0%

Example-V

7-[[(Z)-2-(2-Aminothiazol-4-yl)2-methoxyimino] acetamido]-3-[[(2,5-dihydro-6-hydroxy-2-ethyl-5-oxo-1,2,4-triazin-3-yl)thio]methyl]-3-cephem-4-carboxylic Acid Disodium Hemiheptahydrate (Ceftriaxone Sodium)

7-Amino-3-[[(2,5-dihydro-6-hydroxy-2-methyl-5-oxo-1, 2,4-triazin-3yl)thio]methyl]3-cephem-4-carboxylic acid (20.0 g) was suspended in dichloromethane (200 ml). To this was added hexamethyldisilazane (15.0 g) and trimethylsilyl chloride (3.0 g). The suspension was refluxed for 2–3 hours to get clear solution. Cooled to 0° C. and triethylamine (13.6 g) was added slowly. At the same temperature, 2-mercapto-5-phenyl-1,3,4-oxadiazolyl-(Z)-2-(2-aminothiazol-4-yl) 2-methoxyiminoacetate (23.3 g) was added. The reaction mixture was monitored by HPLC. After completion of reaction, 200 ml water was added and pH was adjusted to 7.0. The aqueous layer was separated, charcoalized and treated with sodium-2-ethylhexanoate (30.5 g) in acetone, reaction was proceeded by same method as mentioned in Ex-IV to get crude ceftriaxone sodium (25.0 g)

Example-VI

3-Acetyloxymethyl-7-[(Z)-(2-aminothiazolyl-4-yl)-2-(methoxyimino)acetamido]-3-cephem-4-carboxylic Acid (Cefotaxime Acid)

A mixture of THF (250 ml) and water (150 ml) and N,N-dimethylacetamide (25.0 ml) was stirred under inert atmosphere. At 0°–1° C., 7-aminocephalosporanic acid (25.0 g) and 2-mercapto-5-phenyl-1,3,4-oxadiazolyl-(Z)-2-(2-aminothiazol-4-yl)2-methoxyimino acetate (39.8 g) were added. Triethylamine (20.4 g) was slowly added to reaction by maintaining pH 7.5 to 8.5. The reaction was followed by HPLC. After 4–5 hrs., the reaction mixture was extracted by methylene chloride. The aqueous layer was subjected to charcoal (0.125 g) treatment. Ethylacetate was added to the filtrate and the solution was acidified with dil. HCl at 10° C. to pH 3.0. The solid separated was filtered, washed with water and ethylacetate and then dried under vacuum at 40–45° C. to get Cefotaxime, 40.9 g (yield 98%).

HPLC (purity)=98–99%

Example-VII

3-Acetyloxymethyl-7-[(Z)-(2-aminothiazolyl-4-yl)-2-(methoxyimino)acetamido]-3-cephem-4-carboxylic Acid (Cefotaxime Acid)

7-Aminocephalosporanic acid (25.0 g) was taken in dichloromethane (200 ml). Hexamethyldisilazane (14.7 g) and trimethylsilyl chloride (5.1 g) were added to it and slurry was refluxed till a clear solution is obtained. The clear solution was cooled to 0° C. and triethylamine (13.9 g) was added to it. At 0° C., 2-mercapto-5-phenyl-1,3,4-oxadiazolyl-(Z)-2-(2-aminothiazol-4-yl)-2-methoxyimino acetate (39.0 g) was added, reaction was monitored by HPLC. After 4–5 hrs., HPLC showed disappearance of 7-amino cephalosporanic acid. Water (200 ml) was added to reaction mixture and pH of mixture was adjusted by triethylamine to 7.0–7.5. The aq. layer was separated and treated with charcoal. Ethylacetate was added to aq. layer and pH was adjusted to 3.0 at 10° C. The solid was filtered and washed with water and ethylacetate. Dried under vacuum at 40° C. to get 36.0 g of cefotaxime acid.

HPLC (purity)=97–98%

Example-VIII

7-[[(Z)-2-(Aminothiazol-4-yl)-(carboxymethoxyimino)acetamido]-3-vinyl-3-cephem-4-carboxylic Acid [Cefixime]

A mixture of THF (200 ml) and water (200 ml) was stirred at 0–1° C. under inert atmosphere, 7-amino-3-vinyl-3-cephem-4-carboxylic acid (21.4 g) and 2-mercapto-5-phenyl-1,3,4-oxadiazolyl-(Z)-[2-(aminothiazol-4-yl) methoxycarbonyl methoxyimino] acetate (46.0 g) were added. Triethylamine (15.1 g) was added slowly and reaction mixture was stirred at 0–5° C. maintaining at pH 7.5 to 8.5. The reaction was monitored by HPLC, after completion of reaction, it was worked up as described in example (V). The wet product is taken in water and treated with aq. sodium hydroxide (7.19 g) solution at 0–2° C. After 10 min., pH was lowered to 7.0 by addition of acetic acid.

The solution was treated with charcoal, filtered and acidified with 1N HCl. Solid precipitated was filtered, washed with water and dried under vacuum to give Cefixime, 36.2 g (yield 80%).

| HPLC (Purity) | 99.5% |
|---|---|

Example-IX

7-[[(Z)-2-(Aminothiazol-4-yl)-2-methoxyimino] acetamido]-3-methyl-3-cephem-4-carboxylic Acid [Cefetamet]

7-Aminodiacetyloxy cephalosporanic acid (2.14 g), active ester, 2-mercapto-5-phenyl-1,3,4-oxadiazolyl-(Z)-2-(2-aminothiazol-4-yl)-2-methoxyimino acetate (3.97 g) were suspended in mixture of THF (tetrahydrofuran) (20 ml) and water (20 ml). TEA was added slowly. The reaction was proceeded in same way as described in example to obtain Cefetamet, 3.65 g (yield 92%).

| HPLC (purity) | 99.0% |
|---|---|

Example-X

7-[[(Z)-2-(Aminothiazol-4-yl)-2-methoxyimino] acetamino]-3-methoxymethyl-3-cephem-4-carboxylic Acid [Cefpodoxime Acid]

7-Amino-3-methoxymethyl-3-cephem-4-carboxylic acid (24.2 g) and 2-mercapto-5-phenyl-1,3,4-oxadiazolyl-(Z)-2-(2-aminothiazol-4-yl)-2-methoxyimino acetate (39.7 g) were suspended in 400 ml of THF and water mixture (1:1). At 10° C. TEA added to maintain pH 7–8. The reaction was monitored and proceeded as described in example IV. To the separated aq. layer, pH was adjusted to 2.7 using 16–18% sulphuric acid. Solid was cooled to 10° C., filtered and washed with water (3×50 ml) and finally with acetone (20 ml) to obtain the Cefpodoxime acid, 37.5 g (yield 88%).

| HPLC (purity) | 98.0% |
|---|---|

Example-XI

7-[[(Z)-2-(Aminothiazol-4-yl)-2-methoxyimino] acetamido]-3-(furanylcarbonyl)thiomethy]-3-cephem-4-carboxylic Acid (Ceftiofur).

7-Amino-3-[(2-furanylcarboxyl)thiomethy]-3-cephem-4-carboxylic acid (3.4 g) and 2-mercapto-5-phenyl-1,3,4-oxadiazolyl-(Z)-2-(2-aminothiazol-4-yl)-2-methoxyimino acetate (4.0 g) were added to a mixture of THF (35 ml) and water (35 ml) at temperature 5° C. The pH of reaction was maintained at 7.5 to 8.5 by addition of TEA during the reaction. After completion of reaction, the reaction was extracted with methylene chloride (25 ml×3). The aqueous layer was diluted with 15 ml THF and pH was lowered to 3 by addition of 1N HCl. The solution is saturated by salt. The organic layer was separated and pH was further adjusted to 0.5 by concentrated HCl. IPE (250 ml) was added to precipitate the hydrochloride salt of Ceftiofur, 4.43 g (yield 79.0%).

| HPLC (purity) | 98.0% |
|---|---|

What is claimed is:

1. A novel derivative of thiazolyl acetic acid represented by the formula (I),

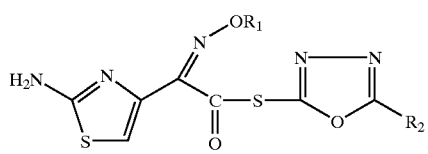
(I)

wherein,
R$_1$ represents H, trityl, CH$_3$, or CR$_a$R$_b$COOR$_3$, in which R$_a$ and R$_b$, independently of one another, represents hydrogen or methyl and R$_3$ represents H or C$_1$–C$_7$ alkyl; and
R$_2$ represents C$_1$–C$_4$ alkyl or phenyl.

2. A process for preparing thiazolyl acetic acid derivative represented by formula (I),

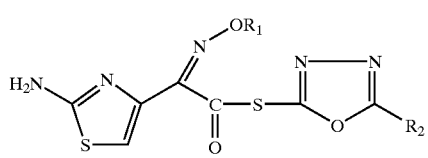
(I)

comprising, reacting a thiazolyl acetic acid represented by formula (IV),

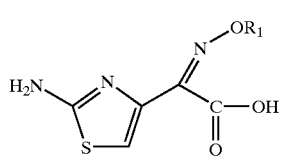
(IV)

wherein,
R$_1$ represents H, trityl, CH$_3$, or CR$_a$R$_b$COOR$_3$, in which R$_a$ and R$_b$, independently of one another, represents hydrogen or methyl and R$_3$ represents H or C$_1$–C$_7$ alkyl;
with thio-oxadiazole of formula (VI),

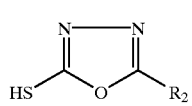
(VI)

wherein, R$_2$ represents C$_1$–C$_4$ alkyl or phenyl;
in the presence of an organic solvent base and a condensation agent, at a temperature being maintained in the range −10° C. to +30° C.

3. The process of claim 2 wherein the organic solvent is selected from dichloromethane, tetrahydrofuran, dioxane, N,N-dimethylformamide, acetone, carbon tetrachloride or mixtures thereof.

4. The process of claim 2 wherein the organic base is selected from triethylamine, diethylamine, tributylamine, pyridine, N-alkylanilines, 1,8-diazabicyclo[5.4.2]undec-7-ene, 1,5-diazabicyclo[4.3.0]non-5-ene, N-methylmorpholine or mixtures thereof.

5. The process of claim 2 wherein the condensation agent is bis-(2-oxo-3-oxazolidinyl)phosphinic chloride.

6. A process for preparing a compound of formula (II),

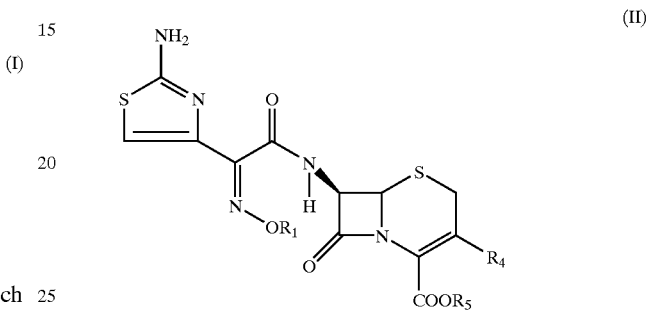
(II)

wherein,
R$_1$ represents H, trityl, CH$_3$, or CR$_a$R$_b$COOR$_3$, in which R$_a$ and R$_b$, independently of one another, represents hydrogen or methyl and R$_3$ represents H or C$_1$–C$_7$ alkyl;
R$_4$ is CH$_3$, —CH=CH$_2$, CH$_2$OCH$_3$, CH$_2$OCOCH$_3$,

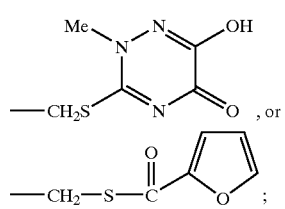
, or

R$_5$ is H or a salt or a carboxylic protecting group; or,

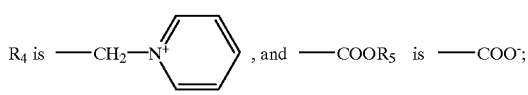

comprising, acylating a compound of formula (III),

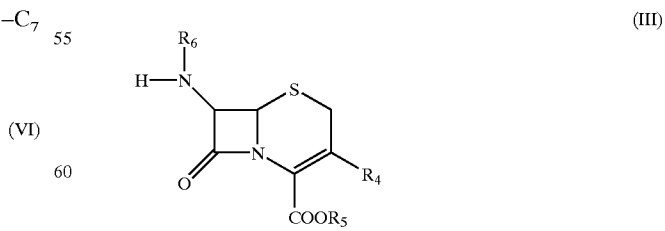
(III)

wherein, R$_4$ and R$_5$ are defined as above, and R$_6$ is H or trimethylsilyl;
with a compound of formula (I),

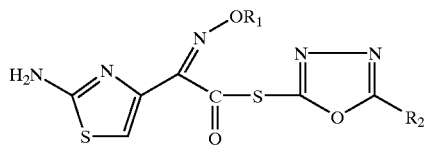 (I)

wherein, $R_1$ and $R_2$ are as defined above;
in the presence of an organic solvent, organic base and a silylating agent at a temperature in the range of $-10°$ C. to $+30°$ C.

7. The process of claim 6 wherein $R_5$ is hydrogen or alkali metal salt.

8. The process of claim 6 wherein said compound of formula II is a syn isomer.

9. The process of claim 6 wherein $R_6$ is H, the acylation is done in the presence of water and an organic solvent selected from the group consisting of tetrahydrofuran, N,N-dimethylacetamide, N,N-dimethylformamide, dioxane, and mixtures thereof.

10. The process of claim 6 wherein $R_6$ is trimethylsilyl, the acylation is carried out in an aprotic organic solvent selected from halogenated hydrocarbon, toluene, or alkyl ether.

11. The process of claim 6 wherein the organic base is selected from the group consisting of triethylamine, N-methylmorpholine, N-methylanilines, 1,5-diazabicyclo[4.3.0]non-5-ene, 1,4-diazabicyclo[2.2.2]octane, 4-dimethylaminopyridine, and mixtures thereof.

12. The process of claim 6 wherein $R_2$ is methyl, $R_4$ is (2,5-dihydro-6-hydroxy-2-methyl-5-oxo-1,2,4-triazin-3-yl) thiomethyl, further comprising purification of this compound by dissolving the crude product in a mixture of water and water miscible organic solvent selected from acetone, isopropyl alcohol, dioxane or mixtures thereof, cooling the solution, separation of impurities from the crude product and precipitation of the purified product.

13. The process of claim 6 wherein $R_2$ is methyl, $R_4$ is (2,5-dihydro-6-hydroxy-2-methyl-5-oxo-1,2,4-triazin-3-yl) thiomethyl, further comprising, the separation of coloured impurities at $-10°$ C. to $0°$ C. by dissolving the crude product in a mixture of water and a water miscible organic solvent, cooling the solution, separation of coloured impurities from the solution and precipitation of the purified product by water miscible organic solvent selected from acetone, isopropyl alcohol, dioxane or mixtures thereof.

14. The process of claim 10, wherein the halogenated hydrocarbon is dichloromethane.

* * * * *